(12) United States Patent
Yi et al.

(10) Patent No.: US 8,615,118 B2
(45) Date of Patent: Dec. 24, 2013

(54) TECHNIQUES FOR TOMOGRAPHIC IMAGE BY BACKGROUND SUBTRACTION

(75) Inventors: Byong Yong Yi, Ellicott City, MD (US); Xinsheng Cedric Yu, Clarksville, MD (US); Jin Zhang, Catonsville, MD (US); Giovanni Lasio, Towson, MD (US)

(73) Assignee: The University of Maryland, Baltimore, Baltimore, MD (US)

( * ) Notice: Subject to any disclaimer, the term of this patent is extended or adjusted under 35 U.S.C. 154(b) by 238 days.

(21) Appl. No.: 13/149,171

(22) Filed: May 31, 2011

(65) Prior Publication Data

US 2011/0293161 A1    Dec. 1, 2011

Related U.S. Application Data

(60) Provisional application No. 61/349,517, filed on May 28, 2010.

(51) Int. Cl.
*G06K 9/00* (2006.01)

(52) U.S. Cl.
USPC ............................ 382/128; 382/131; 382/132

(58) Field of Classification Search
USPC ................................................ 382/128–134
See application file for complete search history.

(56) References Cited

U.S. PATENT DOCUMENTS 6,678,399 B2 * 1/2004 Doi et al. ...................... 382/131
2002/0090119 A1 * 7/2002 Saito et al. .................... 382/128

OTHER PUBLICATIONS

Ding et al., "Accurate patient dosimetry of kilovoltage cone-beam CT in radiation therapy", "Med. Phys.", Feb. 26, 2008, pp. 1135-1144, vol. 35, No. 3.

Guan et al., "Combining various projection access schemes with the algebraic reconstruction technique for low-contrast detection in computed tomography", "Phys. Med. Biol.", 1998, pp. 2413-2421, vol. 43, Publisher: IOP Publishing Ltd, Published in: UK.

Islam et al., "Patient dose from kilovoltage cone beam computed tomography imaging in radiation therapy", "Med. Phys.", Jun. 2006, pp. 1573-1582, vol. 33, No. 6.

(Continued)

*Primary Examiner* — Alex Liew
(74) *Attorney, Agent, or Firm* — Evans & Molinelli PLLC; Eugene J. Molinelli

(57) ABSTRACT

Techniques for background subtraction in computed tomography include determining voxels in a slice of interest in a three dimensional computed tomography scan of the interior of a body based on a first set of measurements of radiation transmitted through the body. Based on the first set of measurements, a first background image for radiation transmitted through the body in a first direction is determined without the effects of the voxels in the slice of interest. A current image is determined based on a different current measurement of radiation transmitted through the body in the first direction. A first difference is determined between the current image and the first background image. The result is a high contrast image in the slice of interest even from a single current projection image.

20 Claims, 14 Drawing Sheets

(56) References Cited

OTHER PUBLICATIONS

Jaffray et al., "Cone-beam computed tomography with a flat-panel imager: Initial performance characterization", "Med. Phys.", Jun. 2000, pp. 1311-1323, vol. 27, No. 6.

Jaffray et al., "Flat-Panel Cone-Beam Computed Tomography for Image-Guided Radiation Therapy", "Int. J. Radiation Oncology Biol. Phys.", 2002, pp. 1337-1349, vol. 53, No. 5, Publisher: Elsevier Science Inc., Published in: US.

Kruger et al., "DigitaK-Edge Substraction Radiography", "Radiology", 1977, pp. 243-245, vol. 125.

Napel et al., "CA Angiography with Spiral CT and Maximum Intensity Projection", "Radiology", 1992, pp. 607-610, vol. 185, No. 2.

Wu et al., "On-Board Patient Positioning for Head-And-Neck IMRT: Comparing Digital Tomosynthesis to Kilovoltage Radiography and Cone-Beam Computed Tomography", 2007, pp. 598-606, vol. 69, No. 2, Publisher: Int. J. Radiation Oncology Biol. Phys.

Yu, Cedric X., "Intensity-modulated arc therapy with dynamic multileaf collimation: an alternative to tomotherapy", 995, pp. 1435-1449, vol. 40, Publisher: Phys. Med. Biol., Published in: UK.

\* cited by examiner

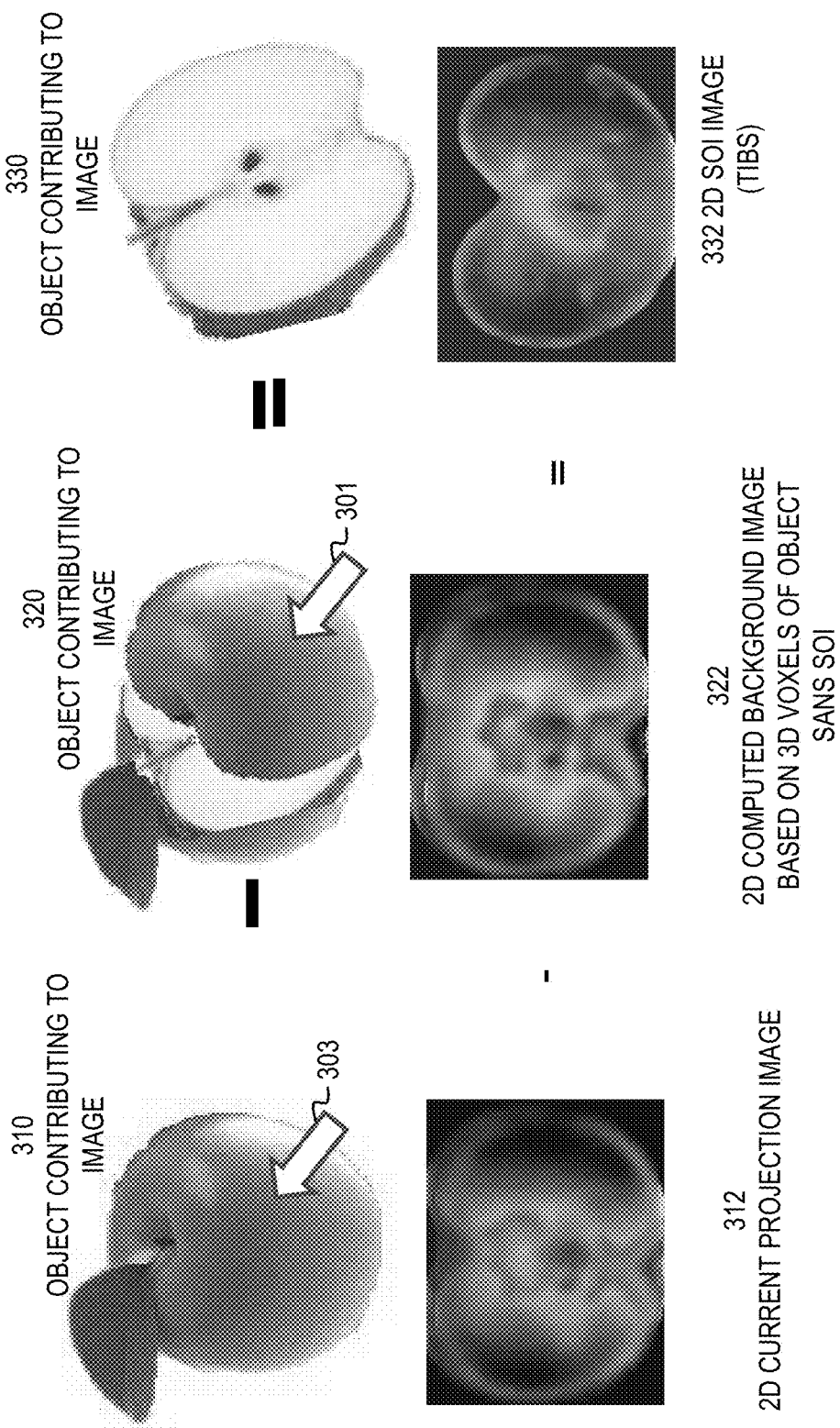

TECHNIQUES FOR TOMOGRAPHIC IMAGE BY BACKGROUND SUBTRACTION

CROSS-REFERENCE TO RELATED APPLICATIONS

This application claims benefit of Provisional Appln. 61/349,517, filed May 28, 2010, the entire contents of which are hereby incorporated by reference as if fully set forth herein, under 35 U.S.C. §119(e).

BACKGROUND OF THE INVENTION

The present invention relates to imaging of the interior of a body using computed tomography (CT). Onboard imaging (OBI) system with kilovoltage X-ray cone beam computed tomography (CBCT) capability allows two-dimensional (2D) and three-dimensional (3D) image guidance for treatment positioning in a body. An X-ray cone beam source is mounted on a gantry that directs the source in multiple directions through a body. The set of acquired projection images are used to infer the 3D distribution of X-ray attenuation in the body using the well known and established principles of computed tomography.

During some procedures it is important to have near real time position information for structures within the body, but full dose 3D imaging is time consuming and increases the exposure of the body to potentially harmful X-ray radiation. Therefore low dose 2D images often are taken for positioning during treatment. Unfortunately, such images include the effects of every structure within the body and contrast for a particular feature of interest is typically lower than in a slice of the full 3D CT imaging.

SUMMARY OF THE INVENTION

Techniques are provided for providing tomographic quality, high contrast images for a slice of interest through a body based on a current measurement, even for a single current projection image, based on subtracting background computed from a previous 3D CT image. These techniques are called tomographic image via background subtraction (TIBS) hereinafter.

In a first set of embodiments, a method includes determining voxels in a slice of interest in a three dimensional computed tomography scan of the interior of a body based on a first set of measurements of radiation transmitted through the body. Based on the first set of measurements, a first background image for radiation transmitted through the body in a first direction is determined without the effects of the voxels in the slice of interest. A current image is determined based on a different current measurement of radiation transmitted through the body in the first direction. A first difference is determined between the current image and the first background image.

In other embodiments, an apparatus or computer-readable medium is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3 is a block diagram that illustrates use of an example 2D image computed from 3D voxels and a current 2D projection image to determine a 2D image of a slice of interest (SOI), according to an embodiment;

DETAILED DESCRIPTION

Figure 1:
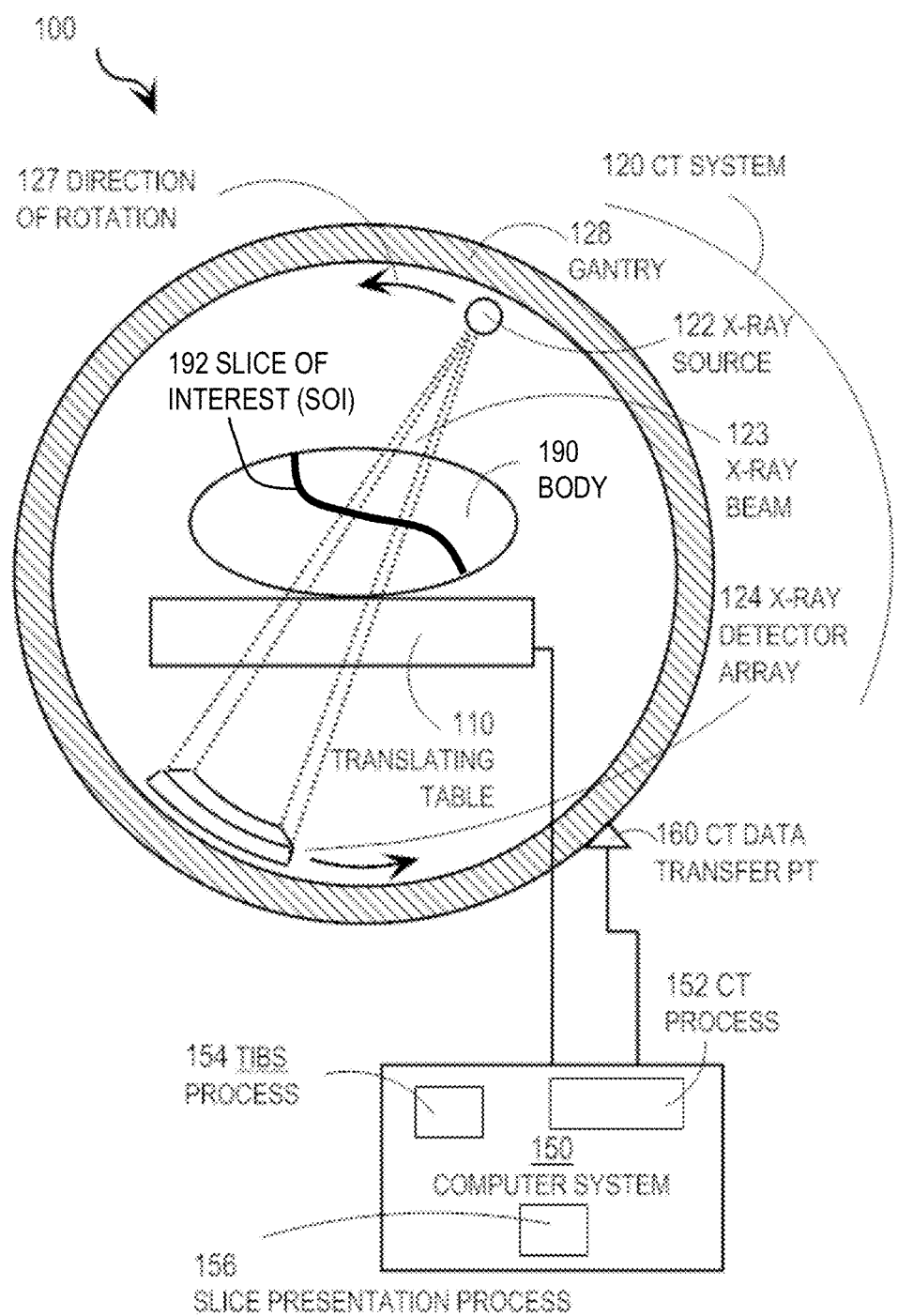
FIG. 1 is a block diagram that illustrates an example system for determining 3D voxels based on CT technology.

Techniques are described for tomographic image via background subtraction (TIBS). In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of X-ray computed tomography (CT) for human bodies. However, the invention is not limited to this context. In other embodiments other subjects or bodies (such as animals, plants and inanimate objects such as packages, machinery, structures, or geologic formations) are probed by the X-ray CT, or other sources of radiation are used, including other electromagnetic waves, acoustic waves or nuclear radiation, alone or in any combination.

1. Overview

The techniques depend on a three dimensional (3D) model of attenuation of radiation in a body. Typically, such a model expresses the radiation attenuation in a volume element, called a voxel. The 3D model is derived from a set of two dimensional (2D) images of radiation intensity, each 2D image measured after passing a beam of radiation from a radiation source through the body in a different direction. Here, body refers to whatever subject is being examined, whether human or not, animate or not. Because the body need not be cut to examine its interior, the technique is said to be non-invasive to the body.

The method then determines the radiation attenuation values for a set of voxels that define a slice through the body. Typically a planar slice one or more voxels thick is selected; but the method works with a curved surface through the body on the order of a few voxels thick.

A background projection image is computed that describes the attenuation of radiation in a particular direction to a projection surface without the attenuation effects by the voxels in the selected slice.

A beam of similar radiation from a radiation source is then passed through the body in the particular direction to provide a current 2D image based on a new measurement, different from that used to construct the 3D model. The background projection image is subtracted from the current 2D image. The result is signal in the 2D image due to the selected slice, because the contributions from the other voxels are in the background image that has been subtracted out.

Thus, the technique includes determining voxels in a slice of interest in a three dimensional computed tomography scan of the interior of a body based on a first set of measurements of radiation transmitted through the body. The technique further comprises determining, based on the first set of measurements, a first background image for radiation transmitted through the body in a first direction without the effects of the voxels in the slice of interest. The technique also includes determining a current image based on a different current measurement of radiation transmitted through the body in the first direction. The technique also includes determining a first difference between the current image and the first background image to show contrast in the slice of interest.

As applied to X-ray radiation, a method to generate computed tomographic quality, high contrast images from a current projected image and a previous CT scan, called tomographic image via background subtraction (TIBS) is described in detail below, and was recently published as Jin Zhang, Byongyong Yi, Giovanni Lasio, Mohan Suntharalingam and Cedric Yu, "Tomographic image via background subtraction using an x-ray projection image and a priori computed tomography," *Med. Phys*, vol. 36, pp 4433-4439, October 2009 (hereinafter Zhang), the entire contents of which are hereby incorporated by reference as if fully set forth herein.

As described below, in some embodiments, it is desirable to register the current image with the background image. Such registration is also desirable in some other embodiments using different subjects or different sources of radiation, or both. Thus, in some embodiments, the technique further comprises registering the current image to the first background image before determining the first difference between the current image and the first background image. Any method may be used to do the registration. In some embodiments, the current image is registered directly with the background image using features apparent in both. In some embodiments, the current image is registered to a corresponding 2D image of the set of two dimensional (2D) images used to derive the 3D model, where the corresponding image is the one in the same projection plane as the current image. Since that corresponding image was used to derive the background image, the current image is indirectly registered to the background image. An advantage of using the corresponding 2D image is that more features would appear in both images. An advantage of using the background image is that, if a structure in the slice of interest has moved, that movement will not affect the registration.

TIBS is extended to transform the difference between the current image and the background image to any arbitrary projection direction. Thus, in some embodiments, the technique further comprises transforming the first difference to a transformed difference in a different direction from the first direction.

2. Structural Overview

2.1 System Structures

FIG. 1 is a block diagram that illustrates an example system 100 for determining 3D voxels based on CT technology. The system 100 includes a CT system 120 and a computer system 150. The system 100 operates on a body 190, such as an animal or human or inanimate object. Although depicted for purposes of illustration, the body 190 is not part of the system 100.

Like most CT systems, CT system 120 includes an X-ray source 122, an X-ray detector array 124, a CT gantry 128 and a translating table 110. In the illustrated embodiment, the CT system 120 includes CT data transfer point 160 and CT process 152 on computer system 150, such as the computer system described below with reference to FIG. 13. In some embodiments the computer system is on board the gantry as one or more chips or ship sets, as described below with reference to FIG. 14

The X-ray source 122 generates an X-ray beam 123 with a particular shape in a particular portion of the X-ray spectrum. The X-ray spectrum is a portion of the electromagnetic spectrum with wavelengths in the range from 10 to 0.01 nanometers, (1 nanometer, nm,=$10^{-9}$ meters) corresponding to frequencies in the range 30 to 30,000 PetaHertz (PHz, 1 PHz=$10^{15}$ Hertz, 1 Hertz=1 cycle per second). The product of the wavelength and the frequency of an electromagnetic wave is the speed of light, a constant, so each different wavelength has a different frequency associated with it. To avoid confusion with other uses of the term frequency, used below, the X-ray spectrum is described herein in terms of its wavelength. The energy of a photon of electromagnetic energy, often expressed in thousands of electron volts (kilo-electron volts, keV) for X-rays, is proportional to the square of the inverse of the wavelength. The shorter wavelengths have the higher photon energies. In the illustrated embodiment, the X-ray source is a dual source that emits X-rays in two distinct portions of the X-ray spectrum. In other embodiments, a single band X-ray source or a spectral X-ray source with more than two portions of the X-ray spectrum is used. In the illustrated embodiment, each X-ray beam is pyramidal shaped, like a thick fan, with a rectangle-like cross sectional area. In other embodiments, electron beams of other shapes are used, such as a thin beam, a thin fan, and a cone.

The X-ray detector array 124 is an array of one or more X-ray detectors sensitive in at least one portion of the X-ray spectral bands emitted by the X-ray source 122. In the illustrated embodiments, the X-ray detector array 124 includes hundreds or thousands of X-ray detectors arranged as a two-dimensional array of rows and columns of detectors. For example, in some embodiments, the X-ray detector array has 128 columns of detectors in each of 256 rows of detectors.

The CT gantry 128 provides a rotational support structure for the X-ray source 122 and X-ray detector array 124 so that an un-diverted X-ray beam 123 from X-ray source 122 impinges on all the detectors in the X-ray detector array 124. In the illustrated embodiment, the gantry 128 rotates in the direction of rotation 127 indicated by a curved arrow at a rate of about three rotations per second. In some embodiments, the X-ray source 122 emits the X-ray beam 123 continuously while rotating and, in some embodiments, the X-ray source pulses the beam 123 so that the beam is off until the detector array 124 has moved to a new position that does not overlap a previous position on the same rotation.

The translating table 110 supports the body 190 at a center of the gantry 128 so that the X-ray beam 123 intersects a volume of interest in the body 190. The translating table also moves the body through the gantry in both directions perpendicular to the plane of FIG. 1, so that a different volume of interest in the body 190 may be positioned to intersect the X-ray beam 123. In some embodiments, the body 190 is supported by a stationary table, and the gantry 128 moves relative to the body in a direction perpendicular to the plane of FIG. 1. In various other embodiments, the translating table also moves the body in a horizontal or vertical direction, or both, in the plane of FIG. 1, so that the correct portion of the body 190 can be illuminated by every beam emitted by the X-ray source during each rotation of the gantry 128.

Based on X-ray intensity (related to the number of X-ray photons that are received) measured at each detector as the detector array completes a circuit of the gantry 128, CT process 152 executing on computer system 150, determines the X-ray absorption properties of each of thousands of volume element in the volume of the body 190 that intersects the X-ray beam 123. X-ray absorption is conventionally expressed in units of Hounsfield (H), named for an early researcher in the field. The size of the smallest volume element for which the system can derive an X-ray absorption value is called the spatial resolution of the system. The spatial resolution of modern helical systems is about 0.3 millimeter (mm, 1 mm=$10^{-3}$ meters) by 0.3 mm by 0.3 mm, for a voxel size of about 0.03 mm$^3$. The temporal resolution is based on the time for one revolution of the gantry, which is about 0.3 seconds, yielding about 3 new scans every second, where a scan includes millions of 0.03 mm$^3$ voxels. The CT transfer point 160 is any mechanism, such as data slip rings, used to transfer CT data from the rotating gantry to computer system 150 for use by CT process 152.

A slice of interest (SOI) 192 is a set of voxels for which high contrast 2D images of absorption are desired at one or more times. The TIBS 154 process executes on computer system 150 to compute a 2D background projection at each of one or more directions based on the 3D voxels, and to subtract that computed 2D background projection from another 2D projection measurement at one or more different times. The resulting TIBS image is presented, stored and or analyzed in the slice presentation process 156 executing on computer system 150.

2.2 Data Structures

Figure 2A:
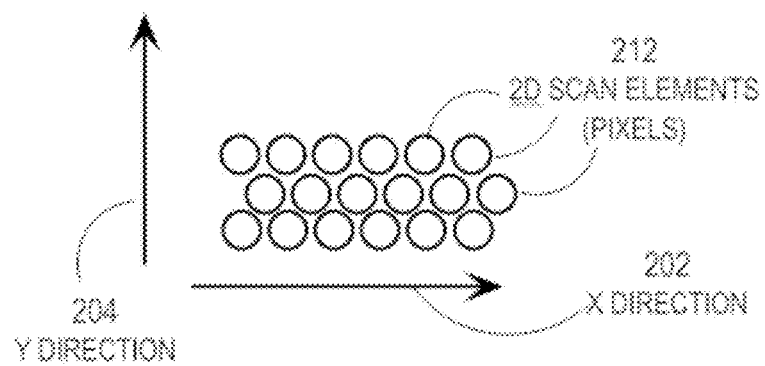
FIG. 2A is a block diagram that illustrates scan elements in a 2D scan, such as one slice from a CT scanner with a one dimensional detector array.

FIG. 2A is a block diagram that illustrates scan elements in a 2D scan 210, such as one slice from a CT scanner with a one dimensional detector array The two dimensions of the scan 210 are represented by the x direction arrow 202 and the y direction arrow 204. The scan 210 consists of a two dimensional array of 2D scan elements 212 each with an associated position. A value at each scan element position represents a measured or computed intensity that represents a physical property (e.g., X-ray absorption) at a corresponding position in at least a portion of the spatial arrangement of the body 190. Although a particular number and arrangement of equal sized circular scan elements 212 are shown for purposes of illustration, in other embodiments, more elements in the same or different arrangement with the same or different sizes and shapes are included in a 2D scan.

Figure 2B:
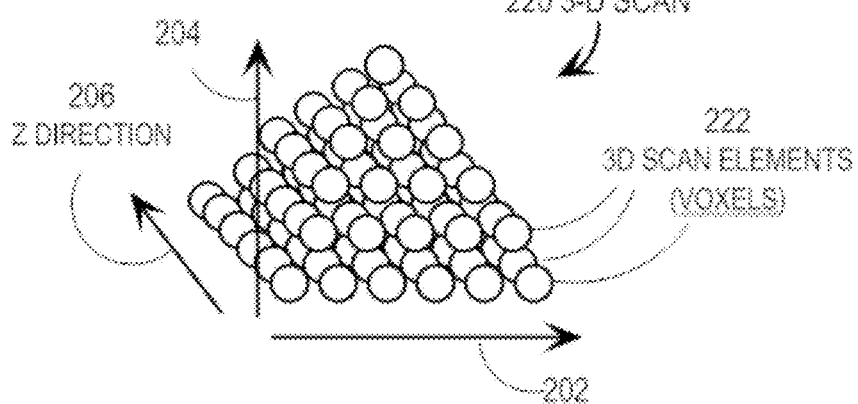
FIG. 2B is a block diagram that illustrates scan elements in a 3D scan, such as stacked multiple slices from a CT scanner with a one dimensional detector array or scan data from one rotation of the CT system of FIG. 1 with a rectangular cross sectional X-ray beam and a two-dimensional detector array.

FIG. 2B is a block diagram that illustrates scan elements in a 3D scan 220, such as stacked multiple slices from a CT scanner with a one dimensional detector array or scan data from one rotation of the CT system of FIG. 1 with a rectangular cross sectional X-ray beam 123 and a two-dimensional detector array 124. The three dimensions of the scan are represented by the x direction arrow 202, the y direction arrow 204, and the z direction arrow 206. The scan 220 consists of a three dimensional array of 3D scan elements (voxels) 222 each with an associated position. A value at each scan element position represents a measured or computed intensity that represents a physical property (e.g., X-ray absorption or acoustic reflectivity) at a corresponding position in at least a portion of the spatial arrangement of the body 190. Although a particular number and arrangement of equal sized spherical scan elements 222 are shown for purposes of illustration, in other embodiments, more elements in the same or different arrangement with the same or different sizes and shapes are included in a 3D scan 220.

In the following, the term voxels is used interchangeably with the term scan elements to mean both 3D scan elements and 2D scan elements that represent measured output from a CT system. A collection of scan elements generated in a particular time interval, such as one revolution of gantry 128, is a scan.

The term image is used herein to indicate a two dimensional set of picture elements (pixels) that are presented on a two dimensional display, such as a cathode ray tube (CRT) display screen or plasma screen or liquid crystal display (LCD) screen, for use by a human viewer, such as the human operator of probe controller 144. In some embodiments, each of one or more image pixels represents data from one or more scan elements (voxels).

Certain voxels in the scan data are associated with a particular object inside the body 190, such as the SOI. The spatial arrangement of the particular object is represented by the set of voxels that are associated with the particular object, or by a boundary between such voxels and surrounding voxels. Such spatial arrangements can be displayed as an image in any number of ways known in the art, such as by segmented cross sections through the object on planes of arbitrary location and orientation, by a 3D rendering of a surface of the object absent other objects, or by the surface of the adjacent tissues absent the particular object.

Various data structures employed in various embodiments include data structures that store: a time series of one or more 2D voxels of X-ray intensity received at one instant on detector array 124 (also called herein an X-ray projection); and a time series of one or more volume scans of X-ray absorption values interior to the body 190 based on CT processing of multiple X-ray projections.

3. Derivation

FIG. 3 is a block diagram that illustrates use of an example 2D image computed from 3D voxels and a current 2D projection image to determine a 2D image of a slice of interest (SOI), according to an embodiment. An object 310 is subjected to penetrating radiation at a variety of angles in order to obtain a 3D CT scan of the object stored as a 3D array of voxel values of some physical property, such as radiation absorption.

At one angle 303, a 2D current projection image 312 is measured (either with a new beam of radiation or relying on one of the beams used to construct the 3D CT scan).

At the same angle 301, the effect of the physical property on the penetrating radiation is computed for all voxels except voxels associated with a slice of interest (SOI), using the equations provided below, to produce the 2D computed background image 322. The computed image 322 represents the result of the penetrating radiation passing through only the portion 320 of the object outside a SOI, as if the SOI had been removed from the object.

The difference provides a high contrast 2D image 332 of the SOI, as if the penetrating radiation passed only through portion 330 of the object coincident with the SOI.

Consider an X-ray point source (e.g., source 122) and a flat panel X-ray detector (e.g., detector array 124). The detected intensity I(s) from primary plus scattered radiation at detector pixel location s is given by Equation 1.

$$I(s)=I_0(s)e^{-P(s)}(1+SPR) \quad (1)$$

where $I_0(s)$ is the incident intensity in the absence of an object (e.g., object 310), and the exponential term represents the attenuation through the object of the primary beam only, and SPR is the scatter-to-primary ratio. The primary beam attenuation is equal to the line integral of the linear attenuation coefficient $\mu(r)$, as given by Equation 2.

$$P(s)=\int_{r\in L}\mu(r)dr \quad (2)$$

where r is the voxel location vector of a voxel inside the object, and L is the X-ray path connecting the X-ray source to the pixel location s. The attenuation coefficient $\mu(r)$ is the physical property of the object at each voxel location r that affects the intensity in the projected image for kilovolt (kV) X-ray fluoroscopes and tomography. The projection images K(s), used as current images or as projections for CT reconstruction, are each a 2D matrix of values calculated as the negative logarithm of the transmission, as given in Equation 3.

$$K(s)=-\ln[I(s)/I_0(s)] \quad (3)$$

In the ideal case where SPR=0, K(s) is equal to P(s). Otherwise the relationship between these two quantities requires the precise knowledge on SPR, which may not be available. If uncorrected, X-ray scatter will cause cup and streak artifacts and inaccurate CT number in reconstructed CT images. High scattered radiation levels are especially problematic in flat-panel based CBCT because beam collimation is extremely challenging for large cone angles. In the Varian OBI system used in experimental embodiments, a significant portion of scatter is rejected by the use of a 10:1 anti-scatter grid and a 50 centimeter (cm, 1 cm=$10^{-2}$ meters) air gap between scan object and detector.

Under the assumption that the position of the patient anatomy at the time of kV imaging is not significantly distorted so that it can be aligned with that of the previous CT scan, the background contents can be considered invariant between the time of the CT scan and kV imaging. In the above situation, the TIBS technique consists of the following major steps.

In a first step, the physical property affecting projections is determined at each voxel location in the object, using principles of computer tomography. Any method known in the art may be used. In the example embodiments described below, an effective attenuation $\mu_{eff}(r)$ is determined at each voxel location r using an algorithm published by L. A. Feldkamp, L. C. Davis, and J. K. Kress, "practical cone-beam algorithm," *Journal of the Optical Society of America*, vol. 1, pp 612-619, 1984 (hereinafter referenced as the FDK algorithm), the entire contents of which are hereby incorporated by reference as if fully set forth herein, except for terminology inconsistent with that used herein. Here, the effective attenuation $\mu_{eff}(r)$ represents the effective X-ray linear attenuation coefficient map that contains cup and streak artifacts and other inaccuracies resulting from scatter and beam hardening.

In a further portion of this first step, the voxels of the slice of interest (SOI) are identified. The voxels not belonging to the SOI are considered as background voxels. A 3D background dataset is created by setting the effective attenuation to zero for the voxels belonging to the SOI, e.g., $\mu_{eff}(r \in SOI)=0$.

In a second step, numerically computed 2D projections (also known as digital reconstructed radiographies, DRRs) in a first direction of the slice of interest (SOI) and background (BKG) are determined according to Equation 4 and Equation 5, respectively.

$$DRR_{SOI}(s)=\int_{r\in L\cap SOI}\mu_{eff}(r)dr \quad (4)$$

$$DRR_{BKG}(s)=\int_{r\in L\cap BKG}\mu_{eff}(r)dr \quad (5)$$

$DRR_{BKG}(s)$ is used as the 2D computed background image (e.g., image 322). In some embodiments, $DRR_{SOI}(s)$ is used as reference image or for verification, or some combination.

In a third step, $DRR_{BKG}(s)$ is subtracted from a 2D current projection image (e.g., image 312) to obtain a TIBS image (e.g., 2D SOI image 332), as given by Equation 6.

$$TIBS_{SOI}(s)=K(s)-DRR_{BKG}(s) \quad (6)$$

Under ideal conditions, $TIBS_{SOI}(s)$ is equivalent to $DRR_{SOI}(s)$.

In practice, for kilovolt X-ray wavelengths, the imaging setup for the 2D current projection image may not be perfectly aligned with the setup (e.g., FIG. 1) of the CT scan. In such cases, an image registration step is included between the above second and third steps, to align as much as possible the K(s) and $DRR_{BKG}(s)$ 2D images.

Figure 4:
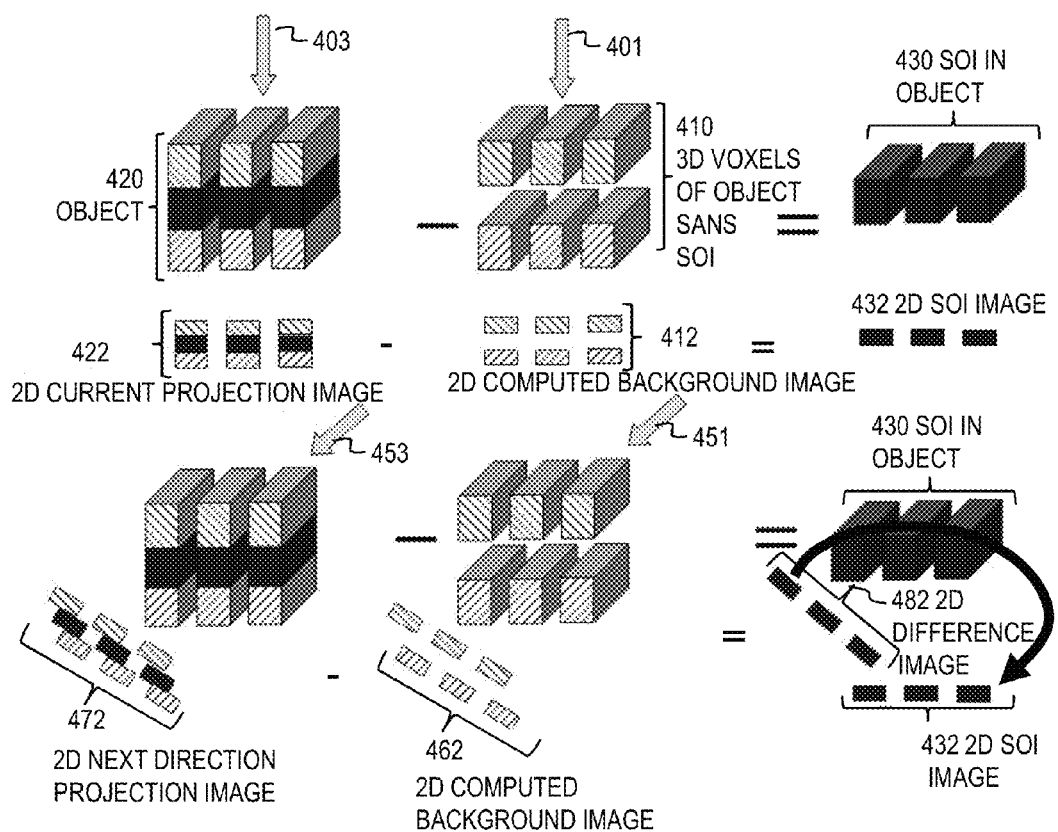
FIG. 4 is a block diagram that illustrates use of an example 2D imaged computed from 3D voxels and a current 2D projection image in a different direction to determine a 2D SOI according to an embodiment.

FIG. 4 is a block diagram that illustrates use of an example 2D imaged computed from 3D voxels and a current 2D projection image in a different direction to determine a 2D SOI according to an embodiment. As in FIG. 3, an object 410 is subjected to penetrating radiation at a variety of angles in order to obtain a 3D CT scan of the object stored as a 3D array of voxel values of some physical property, such as radiation absorption. At one angle 403, a 2D current projection image 422 is measured (either with a new beam of radiation or relying on one of the beams used to construct the 3D CT scan) that includes the effects of the combined absorption of all portions of the object 420. At the same angle 401, the effect of the physical property on the penetrating radiation is computed for all voxels except voxels associated with a slice of interest (SOI), using the equations described above, to produce the 2D computed background image 412. The computed image 412 represents the result of the penetrating radiation passing through only the portion 410 of the object outside a SOI, as if the SOI had been removed from the object. The difference provides a high contrast 2D image 432 of the SOI, as if the penetrating radiation passed only through portion 430 of the object coincident with the SOI.

To compute the same 2D SOI image 432 from a measurement at a different angle 453, a 2D current projection image 472 is measured (either with a new beam of radiation or relying on one of the beams used to construct the 3D CT scan) that includes the effects of the combined absorption of all portions of the object 420. At the same angle 451, the effect of the physical property on the penetrating radiation is computed for all voxels except voxels associated with the SOI, using the equations described above, to produce the 2D computed background image 462. The computed image 462 represents the result of the penetrating radiation passing through only the portion 410 of the object outside a SOI, as if the SOI had been removed from the object. The difference provides a high contrast 2D image 482 of the SOI, as if the penetrating radiation passed only through portion 430 of the object coincident with the SOI at angle 451. The difference image 482 is then transformed to a different direction 401, using the steps described below, to produce a high contrast 2D image 432 of the SOI in direction 401. The steps involve determining the property values of the SOI in the object 430 and then computing the propagation of the radiation through the SOI in the new direction 401, as indicated by the bold arrow.

The process of transforming from direction θ1 to a different direction θ2 is called filtered back-projection and reconstruction of subtracted thin slice (FAROSTS) and includes the following steps:

a. At angle θ1 define an SOI and divide the SOI into n subslices perpendicular to θ1.
b. Generate a TIBS for each subslice at θ1, and call these subslice differences Ti (i=1,2 ... n).
c. Perform filtered back-projection (FBP) on each Ti onto its corresponding position in the image space, to form one final synthesized image I of the SOI, still at θ1: I=ΣFBPθ1{Ti}.
d. At the desired direction angle θ2 perform the forward projection on image I, i.e., T=Proj θ2 {I} to obtain TIBS of the SOI at θ2.

4. Method

Figure 5:
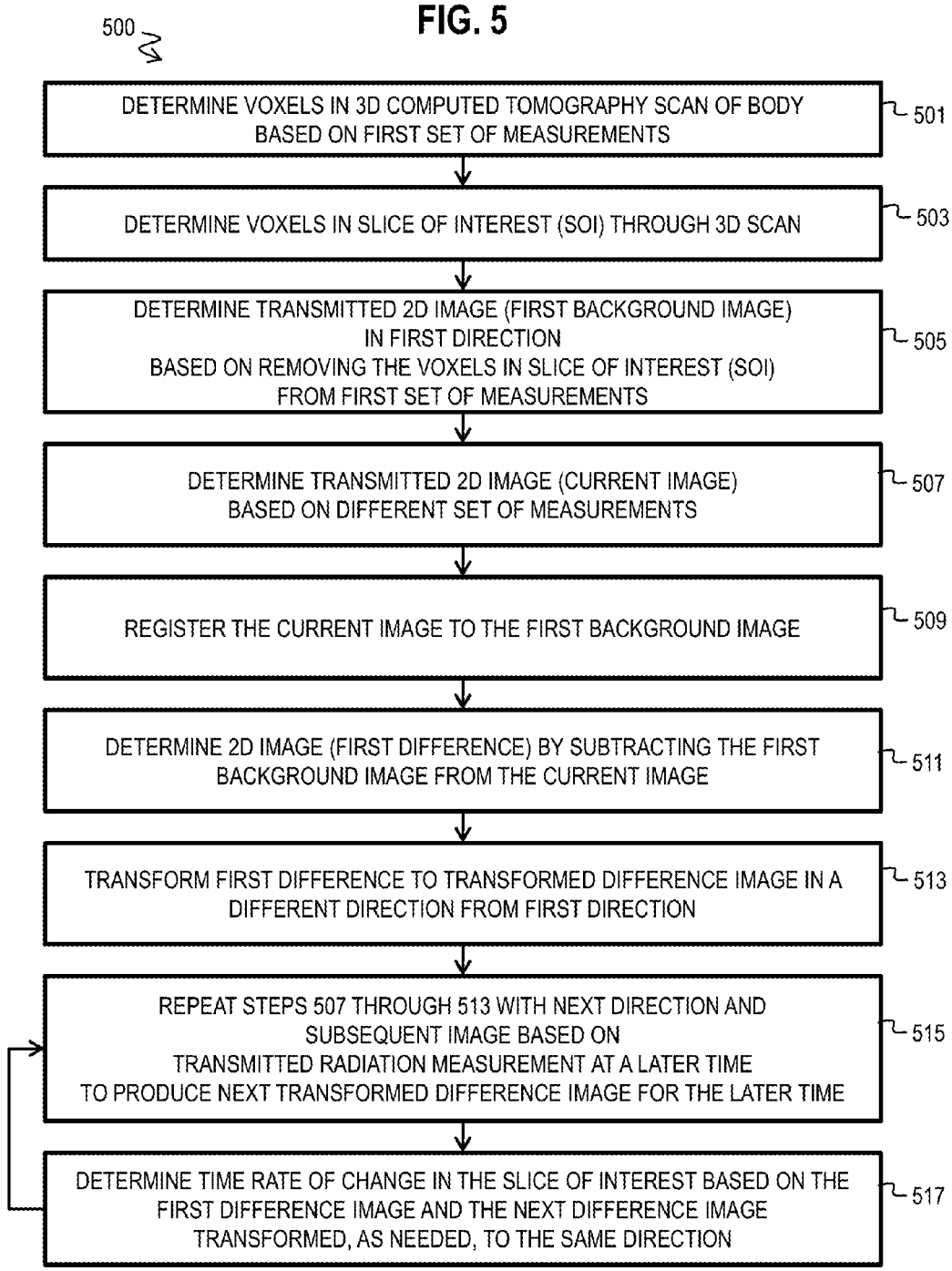
FIG. 5 is a flow diagram that illustrates at a high level an example method of using CT to compute one or more 2D images of a SOI according to an embodiment.

FIG. 5 is a flow diagram that illustrates at a high level an example method 500 of using CT to compute one or more 2D images of a SOI. Although steps in FIG. 5 are shown in a particular order for purposes of illustration, in other embodiments, one or more steps may be performed in a different order or overlapping in time, in series or in parallel, or one or more steps may be omitted or added, or changed in some combination of ways.

In step 501, the voxels in 3D computed tomography scan of a body are determined based on first set of measurements at a variety of angles and the principles of computed tomography, well known in the art. This step includes the only high dose exposure to radiation that the body is subjected to during the method. In some embodiments, step 503 includes operating the CT system, such as CT system 120 of FIG. 1 to acquire the first set of measurements. In some embodiments, the voxels are obtained from a data source, such as a storage disc or as signals over a network.

In step 503, the voxels in the SOI are determined. For example, the voxels in SOI 192 are determined.

In step 505, transmitted 2D image (first background image) in a first direction is determined based on removing the voxels in SOI from first set of measurements. For example, 2D computed background image 412 is determined in direction 401, using the equations described above.

In step 507, a radiation transmitted 2D image (current image) is determined based on a different set of measurements. The radiation transmission direction is in the same as the first direction used to compute the background image. In some embodiments, the different set of measurements is a single projection image in the first direction from the multiple images collected during the CT scan. In some embodiments, the different set of measurements is a new projection image, such as a single new low dose fluoroscopic X-ray image taken in the first direction. For example, 2D current projection image 422 is obtained.

In step 509, the current image is registered to the first background image. Any method may be used, including manual aligning of the two images, or sophisticated computational methods for maximizing a measure of similarity. For example, 2D current projection image 422 is registered to the 2D computed background image 412 (without the SOI) or a projection image of the CT scan in the same direction that includes the SOI. In some embodiments, such as embodiments that use one of the projection images from the multiple images of the CT scan, step 509 is omitted.

In step 511, a 2D image (first difference) is determined by subtracting the first background image from the current image. For example, 2D SOI image 432 is obtained by subtracting 2D computed background image 412 from 2D current projection image 422.

In step 513, the first difference image is transformed to transformed difference image in a different direction from first direction. For example, the 2D difference image 482 is transformed to the 2D SOI image 432, as described above. In some embodiments, in which the direction of the current projection image is the desired target direction, step 513 is omitted. For example, if 2D current projection image 422 was measured in the desired target direction 403, then the first difference 2D SOI image 432 is the desired image, and step 513 is omitted.

In step 515, steps 507 through 513 are repeated with next direction and subsequent image based on transmitted radiation measurement at a later time, if any, to produce next transformed difference image for the later time. For example, a low dose fluoroscopic X-ray image is taken in the same direction 401 after one or more days, weeks or months, to determine the progression of a feature in the SOI over time. Similarly, in some embodiments, the progression of a feature over the time of the CT scan itself (several minutes) is determined based on transforming the SOI images 482 measured in different directions 453 seconds apart to the desired target direction 401, as described in more detail below.

In step 517, the time rate of change in the slice of interest is determined based on the first difference image and the next difference image transformed, as needed, to the same direction. For example the velocity of a ball in an image phantom described below, or growth rate of a tumor or sinus cavity, is determined based on the series of 2D images of the SOI.

In some embodiments for which a time series of the SOI is not desired, step 515 and step 517 are omitted, and the process ends, in various embodiments, with step 511 or with step 513.

5. Experimental Embodiments

5.1 Phantom Embodiments

Figure 6:
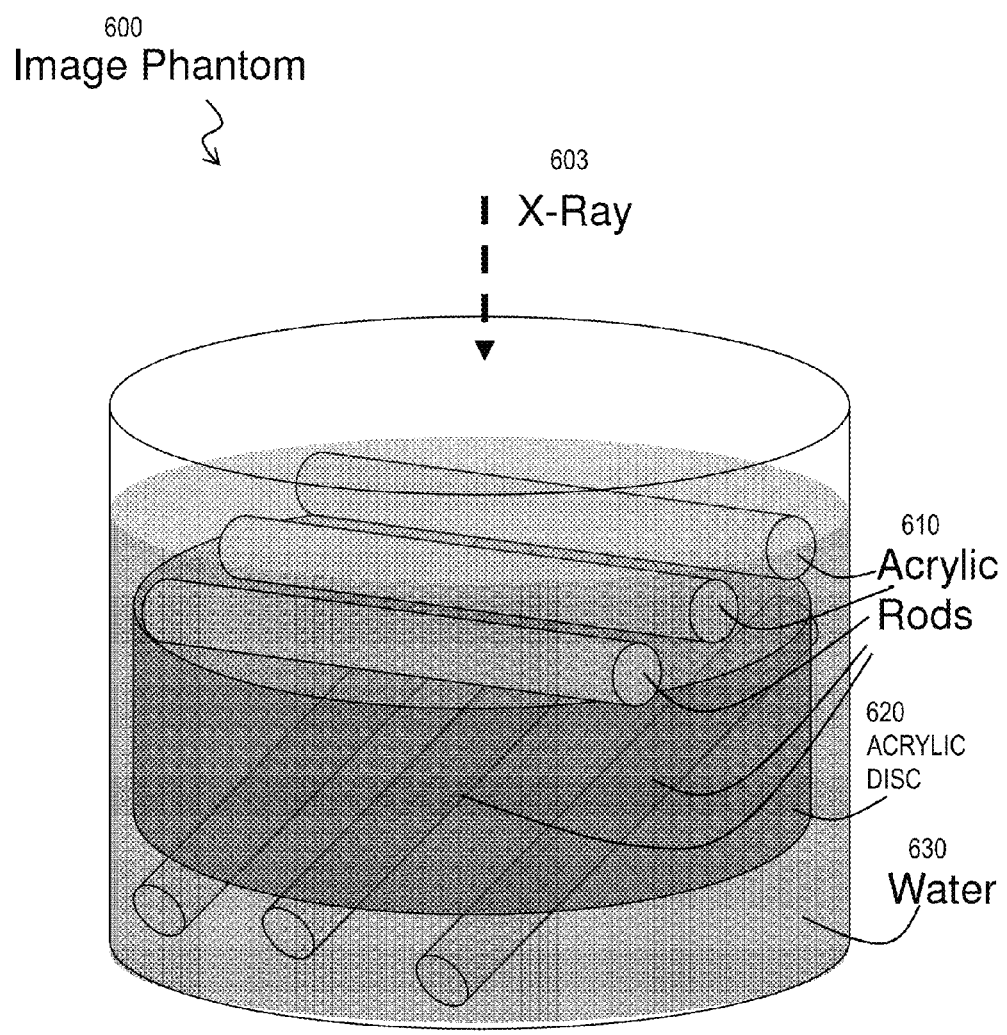
FIG. 6 is a block diagram that illustrates an example physical arrangement to generate an image phantom for demonstrating one or more steps of the method of FIG. 5 according to an embodiment.

FIG. 6 is a block diagram that illustrates an example physical arrangement to generate an image phantom 600 for demonstrating one or more steps of the method of FIG. 5 according to an embodiment. The image phantom 600 includes acrylic rods 610 in two orientations separated by an acrylic disc 620, all immersed in water 630. All materials have similar radiation absorption properties to each other and human organs at kilovolt X-ray wavelengths. Demonstrations were performed with X-ray beam direction 603.

TIBS was implemented using an on-board imaging (OBI) system on a linear accelerator (Trilogy, Varian Medical Systems, Palo Alto, Calif.). Two phantoms (phantoms 1 and 2) were designed with six polymethyl methacrylate (PMMA) rods 610 and two disk modules 620 of a disassembled CATPHAN® phantom (The Phantom Laboratory, Salem, N.Y.). The six PMMA rods are all 15 cm long and 1.2 cm in diameter; and the two disk modules are both 15 cm in diameter and 2.4 and 4 cm thick, respectively. For phantom 1, a sensitometry module of the CATPHAN® phantom and the six rods were placed in a water filled plastic bucket 21 cm in diameter and 14 cm in height. As shown in FIG. 6, three rods were placed on top of the disk module along the couch [superior-inferior (SI)] and the other three were placed below the disk perpendicular to the couch [left-right (LR)]. The imaging isocenter was placed around the center of the disk module.

The sensitometry module contains eight cylindrical inserts made of different materials. The projections of the eight cylinders in the anterior-posterior (AP) direction were circular regions on the kV image and on the subtracted slice image. These regions were used to measure relative contrast-to-noise ratios (CNR). CNR is a simple and objective measure of the detectability of certain structures with uniform intensity. It is defined by Equation 7.

$$CNR = |Sin - Sout| / \sqrt{(\sigma in^2 + \sigma out^2)} \quad (7)$$

where Sin and Sout are the averaged image pixel intensities within a given region of interest (ROI) and a uniform background region outside the ROI, respectively. The quantities σin and σout are the standard deviations of noise inside and outside the ROI, respectively.

Phantom 2 was designed in the same way as phantom 1 except that a low-contrast disk module replaced the sensitometry one to test the low-contrast visibility in TIBS images.

Projection data for CBCT reconstruction were acquired using a 40×30 cm² PAXSCAN® 4030CB onboard flat-panel imager (OBI, Varian Medical Systems, Palo Alto, Calif.). Each set of projection data contains 1024×768 pixels where each pixel covers a 0.388×0.388 mm² area, (1 mm, millimeter, =10⁻³ meters). A CBCT acquisition consisted of about 630 evenly distributed view angles over a complete circle of 360°, with a "standard" technique of 125 kVp, 80 mA, and 15 ms, a source-to-axis distance (SAD) of 100 cm, and source-to-detector distance (SDD) of 150 cm. All CBCT scans were operated under the full-fan (i.e., 25 cm diameter field of view or less) CBCT mode with a 10:1 anti-scatter grid and a bow-tie filter mounted. The kV images used were selected among the projections acquired during the CBCT scan. By acquiring the kV images with the same technique, filtering condition, and geometric setup, misalignments between CBCT and kV images, as well as possible differences in the data normalization, are eliminated. In order to demonstrate the effects of geometrical misalignment on TIBS results, an intentionally shifted kV image set was generated before applying the TIBS technique in some embodiments.

The projection data from the CBCT scans were subjected to dark/flood-field calibration and bad-pixel correction. These projections were then divided by the projection of a normalization cylindrical phantom (NORM-phantom) whose density $\mu_0(r)$ is expected to be close to that of the scan object. This normalization procedure is essentially equivalent to Eq. (3) where $I_0(r)$ is the NORM-phantom attenuated intensity instead of "open-field" reading; and, it helps reduce the effects of scatter and beam hardening. Finally the natural logarithm was performed on the ratio of the intensities to form the projection data K(s). CBCT voxels corresponding to the relative linear absorption coefficients $(\mu_{eff} - \mu_0)$ were reconstructed using the FDK algorithm with Blackman filter. (Unless otherwise specified, kV images and CBCT projections are after NORM-phantom normalization and logarithm transformation. Reconstructed CBCT voxel values represent relative absorption coefficients). The 3D CBCT volume matrix contains 400 axial slices with 0.55 mm slice thickness; each slice is a matrix of 600×600 pixels with size of 0.46×0.46 mm². Neither x-ray scattering nor beam hardening was corrected in the reconstruction algorithm because much of the effect is reduced in the subsequent subtraction during TIBS. An SOI was selected in the reconstructed CBCT volume, and the BKG was created by setting the SOI voxel values to zero. Voxels belonging to BKG were projected onto a 2D 1024×768 pixel simulated flat-panel detector using a standard ray-driven forward projection method to generate $DRR_{BKG}$. The subtracted result $TIBS_{SOI}$ was obtained by subtracting $DRR_{BKG}$ from the kV image. Theoretically, the resulting TIBS image contains only the information in SOI and closely mimics the reference image $DRR_{SOI}$.

The results for phantom 1 included three coronal TIBS slices obtained from one kV image, using three different backgrounds. The image of the three SI direction rods over the sensitometry module can be seen, while the sensitometry module and other three rods almost disappeared in the 1.3 cm thick coronal TIBS slice. Likewise, the same slice thickness of TIBS at different levels contains the other three LR direction rods. It shows similar result of removing most of the information from the other three rods and the sensitometry module. In a 2.4 cm TIBS slice that contains the whole sensitometry disk; all the sensitometry inserts are clearly visible (1-8 clockwise) including the one with the lowest contrast (3) that is hardly discernable on the original kV image. To allow for fair comparison, the window/level for both kV image and subtracted slice are carefully adjusted so that both images have respective optimal W/L in displaying the targeted structures. Note that all TIBS images still contained shadows from background structures; nevertheless, they provided a cleaner image of structures within the selected SOI. Profiles through the images of the sensitometry disk, drawn through the center of inserts 4 and 6 for the images of kV $DRR_{BKG}$ and their difference $TIBS_{SOI}$ were determined.

The disks that were not overlapping with any shadows of background PMMA rods were selected to compute CNRs. We chose insert 1 and 5 and drew two same sized circles completely inside each sensitometer as ROIs. Two same sized circles were drawn in the vicinity and completely outside each sensitometer. For insert 1, the subtracted slice has CNR=7.27 compared to CNR=1.33 in the kV image, representing a 5.5-fold increase. For insert 5, the subtracted slice has CNR=28.98, compared to CNR=11.14 in the kV image, a 2.6-fold increase. The CNRs calculated from the reference images $DRR_{SOI}$ are 18.7 and 105.9 for inserts 1 and 5, respectively.

The low-contrast inserts within phantom 2 were used to test the soft-tissue detectability with the TIBS technique. A 2.4 cm thick SOI containing inserts of different sizes and contrasts was selected and extracted from the kV image. The TIBS image showed at least seven discernable low-contrast inserts ranging from 1.5 down to 0.4 cm in diameter. The seven visible disks correspond to inserts with contrast of 1%. The other inserts, with 0.5% or lower contrast were not visible in the TIBS image. Several inserts with 0.5% contrast can be recognized on the reference image $DRR_{SOI}$. 1% difference in x-ray absorption coefficient represents soft-tissue contrast range, and it is not surprising to observe none of these seven inserts on the kV image.

Now consider the practical case where kV imaging setup is not perfectly aligned with that of the CBCT scan. The kV image was intentionally shifted from its original position by ~1.5 mm in both SI and LR directions in the imaging plane, which mimics rigid-body setup errors prior to the application of TIBS technique. The background $DRR_{BKG}$ was subtracted from the shifted kV image and three slices were obtained. Compared to their corresponding ideal TIBS images, it was found that misaligned background manifests as edge-enhanced structures ghosting on the final displayed TIBS image. It is also observed that the level of edge-ghosting artifacts proportionally depends on the size and contrast of the misaligned background components (e.g., the bigger size or higher contrast the misaligned components are, the heavier edge-ghosting artifacts are displayed in the subtraction).

As previously described, solution to this problem is to apply an image registration before subtracting $DRR_{BKG}$ from kV image. In the phantom experiment where the kV image is artificially translated in the imaging plane, a 2D rigid-body image registration would suffice to correct for the mismatch between kV and $DRR_{BKG}$.

5.2 Head and Neck Embodiments

TIBS was tested with a head and neck case. The CBCT scan was operated under the full-fan mode with bow-tie filter mounted. CBCT projection data were acquired at about 600 different view angles using the PAXSCAN® 4030CB imager.

First the feasibility of TIBS was demonstrated under ideal condition, where setup errors and data normalization mismatches were absent between CBCT and kV images. Two projections were retrospectively selected from the same CBCT dataset to be used as AP and LR direction kV radiographic images. In this ideal and somewhat unrealistic scenario, the TIBS technique was repeated on five sets of CBCT data that correspond to weeks 1-5 of the treatment course. All five CBCT datasets were normalized to the NORM-phantom and logarithm-transformed, and kV images of each week were taken from their corresponding same week CBCT dataset.

The feasibility of TIBS in a more realistic scenario was also tested, in which week 2 CBCT was used as a priori information and projections of week 3 CBCT were used as the LR kV images acquired on the treatment day (1 week after previous CBCT was taken). Geometrical mismatch existed between the kV images and CBCT dataset due to setup errors. A 2D rigid-body registration between the week 3 kV image and week 2 DRR image was applied to correct setup errors before applying subtraction. Image registration software was used as described by S. M. Smith, M. Jenkinson, M. W. Woolrich, C. F. Beckmann, T. E. J. Behrens, H. Johansen-Berg, P. R. Bannister, M. De Luca, I. Drobnjak, D. E. Flitney, R. Niazy, J. Saunders, J. Vickers, Y. Zhang, N. De Stefano, J. M. Brady, and P. M. Matthews, "Advances in functional and structural MR image analysis and implementation as FSl)," *Neuroimage* vol. 23, number S1, pp 208-219, 2004 (hereinafter referenced as FSL), the entire contents of which are hereby incorporated by reference as if fully set forth herein except for terminology inconsistent with that used herein. The 2D-2D three-parameter rigid registration method was selected in the FLIRT function, which considers two translation components and one rotation angle within the 2D imaging plane. FLIRT is described by M. Jenkinson and S. M. Smith, "A global optimization method for robust affine registration of brain images," *Med. Image Anal.* vol. 5, Number 2, pp 143-156, 2001, the entire contents of which are herby incorporated by reference as if fully set forth herein except for terminology inconsistent with that used herein.

A 2 cm thick sagittal SOI and a 2 cm coronal SOI were selected in a CBCT image volume of a head and neck patient, in which case the tumor resides in the sphenoid sinus. TIBS images were generated by subtracting background DRR images from the right lateral and the anterior kV images, respectively.

Figure 7:
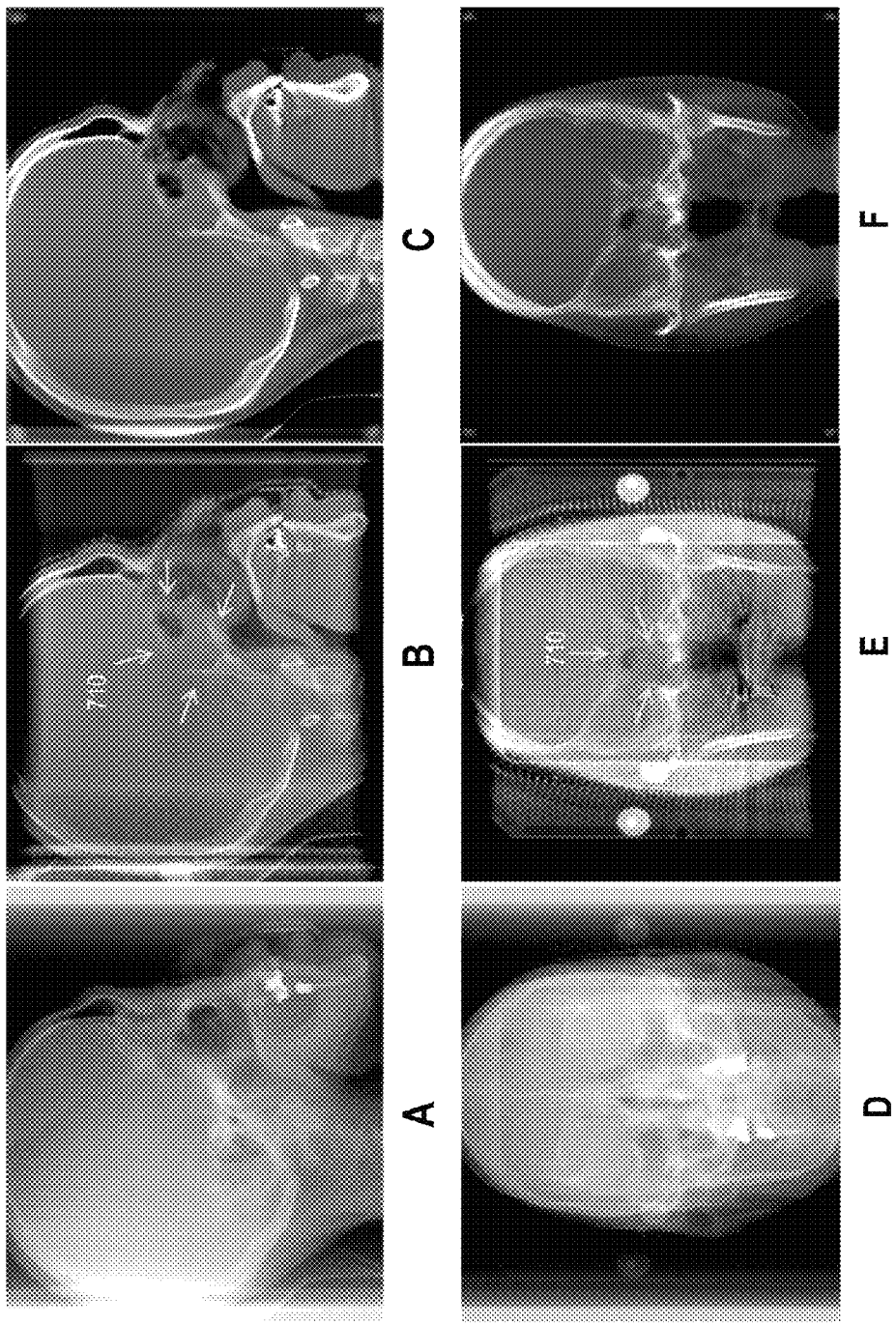
FIG. 7 is a set of example 2D images that illustrates one or more steps of the method of FIG. 5 for a kilovolt X-ray radiation of a head and neck target in left-right and anterior-posterior directions; according to various embodiments.
Figure 8:
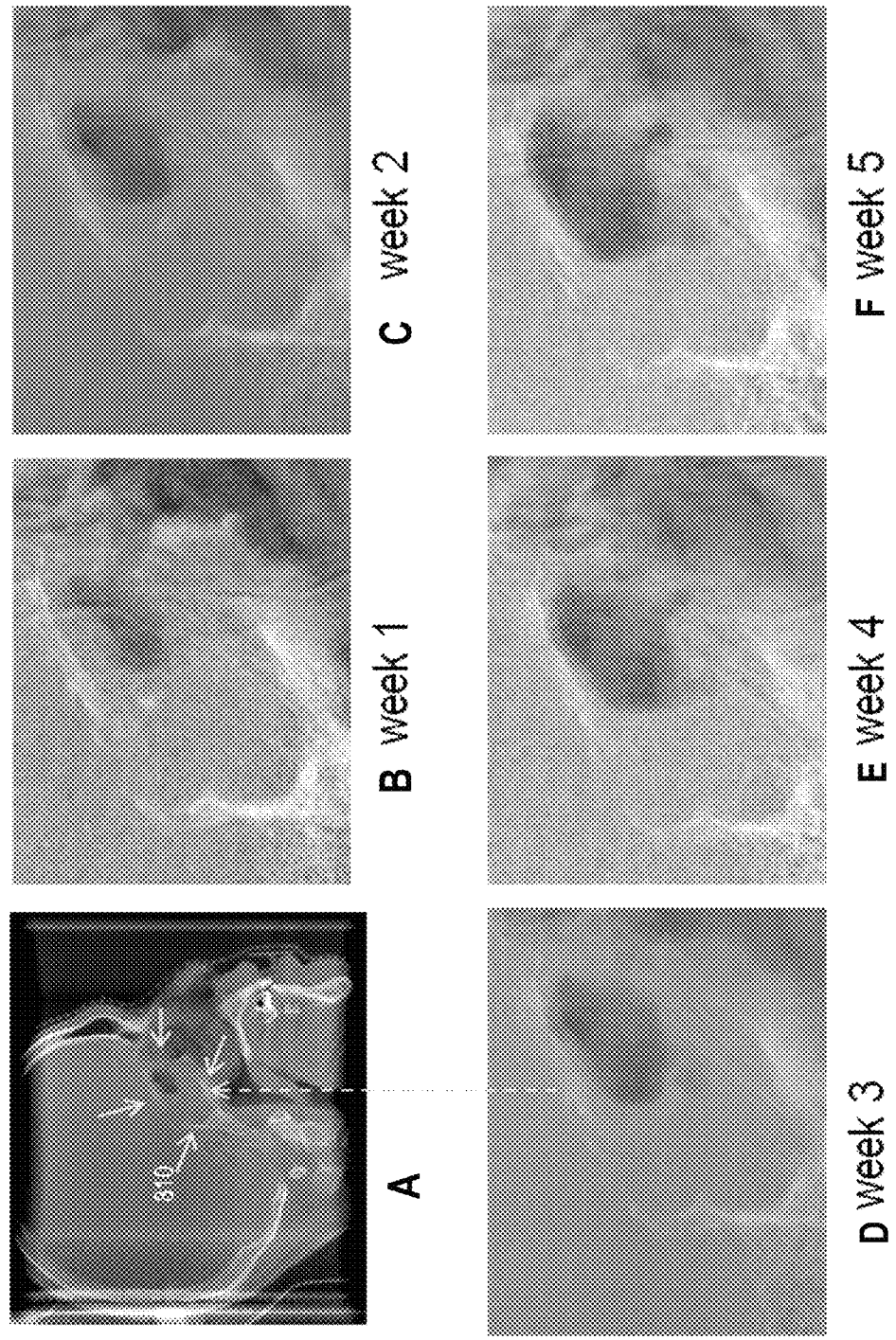
FIG. 8 is a set of example 2D images that illustrates one or more steps of the method of FIG. 5 for a kilovolt X-ray radiation of a head and neck target at multiple subsequent times, according to an embodiment.

FIG. 7 is a set of example 2D images that illustrates one or more steps of the method of FIG. 5 for a kilovolt X-ray radiation of a head and neck target in left-right and anterior-posterior directions; according to various embodiments. FIG. 7A and FIG. 7D depict kV images in the sagittal and coronal directions, respectively. FIG. 7B and FIG. 7E depict TIBS images in the sagittal and coronal directions, respectively. FIG. 7C and FIG. 7F depict reference images in the sagittal and coronal directions, respectively. Reference images are the projections of the SOIs isolated from the CBCT image. A target area is pointed by arrows 710. FIG. 8 is a set of example 2D images that illustrates one or more steps of the method of FIG. 5 for a kilovolt X-ray radiation of a head and neck target at multiple subsequent times, according to an embodiment. Thus, FIG. 8 depicts a series of TIBS images zoomed on the target region 710 from different weeks of the treatment course (weeks 1-5). Increasing air volume in the sinus cavity is observed from the sequence of images. By choosing kV images from the same week CBCT datasets, all TIBS images are created assuming no setup errors.

Under the ideal situation of no registration errors, kV images are a subset of the (week 3) CBCT data. Compared to their corresponding kV images FIG. 7A and FIG. 7D, the TIBS images FIG. 7B and FIG. 7E, respectively, display little background information similar to the reference images, i.e., the projections of the SOIs isolated from the CBCT image FIG. 7C and FIG. 7F, respectively. The background-subtracted sagittal and coronal slices have superior image quality over the corresponding LR/AP kV images and better defined anatomical information on the SOIs. The arrows in FIG. 7B and FIG. 7E delineate the sinus cavity region where a tumor resides; the tumor/air interface can be easily identified in the TIBS images while not in original kV images FIG. 7A and FIG. 7D. A series of TIBS images zoomed on the target region is displayed in FIG. 8, where kV images were, respectively, taken from the corresponding week CBCT datasets, weeks 1-5. The air volume in the sinus cavity increased as treatments progressed, a clear indication of tumor shrinkage due to radiation therapy. Note that the images of weeks 1, 4, and 5 look noisier than those of weeks 2 and 3; this is because the CBCTs were acquired in "low-dose" mode in weeks 1, 4, and 5, which reduce the imaging dose to about one-fifth of that of the "standard-dose" mode in weeks 2 and 3. In both dose levels, TIBS images show improved image quality compared to their corresponding kV image.

Figure 9:
FIG. 9 is a set of example 2D images that illustrates one or more steps of the method of FIG. 5 for a kilovolt X-ray radiation of a head and neck target using registration, according to an embodiment.

FIG. 9 is a set of example 2D images that illustrates one or more steps of the method of FIG. 5 for a kilovolt X-ray radiation of a head and neck target using registration, according to an embodiment. A geometrical mismatch existed between the kV imaging and CBCT dataset in this embodiment. FIG. 9A depicts direct subtraction, without registration. TIBS image contains edge-ghosting artifacts due to mismatched background. FIG. 9B depicts subtracted TIBS image, after rigid-body components of the misalignment is corrected by image registration software FSL. FIG. 9B depicts LR direction kV image Week 2.

CBCT was used as a priori information, while projections of week 3 CBCT were used as the LR kV images acquired on the treatment day (1 week after previous CBCT was taken). When direct subtraction was performed, TIBS images FIG. 9A contained edge-ghosting artifacts due to mismatched background. To reduce these artifacts, a 2D rigid-body registration between the week 3 kV image and week 2 DRR image was used. The image registration considers two translation components and one rotation angle within the 2D imaging plane. The registration result from the FSL software indicated a 1.57 mm AP direction shift and a 1.97 mm SI direction shift on the imaging plane and nearly no rotation between week 3 kV image and week 2 DRR image. This corresponds to 1.04 and 1.3 mm isocenter shift in the AP and SI directions, respectively, between the two treatment sessions. After this translational mismatch was accounted for, TIBS image FIG. 9B provides considerably better image quality compared to direct subtraction result FIG. 9A, and it provides more accurate SOI than the conventional kV image FIG. 9C.

6. Fluoroscopic Time Sequence

Often a fluoroscope is used to determine current position of structures inside a body, especially for a body during a treatment procedure. The fluoroscope provides a projection image that is updated frequently in time to track motion of structures in the body.

A fluoroscopic time sequence can be derived by subtracting the same background from a time sequence of low dose radiation images taken from a fixed direction.

In some embodiments, advantage is taken of the sequence of 2D images on different projection planes provide by a rotating gantry in an on-board imaging (OBI) system. Each 2D image is acquired at a different time and different direction. A difference from each 2D image can be obtained using a different computed background image for different directions through the same selected slice of interest. Using the methods of transforming differences to an arbitrary direction, all these difference can be transformed to the same target direction. As a result, the time series of different 2D images at different direction can be converted to a time series of the differences representing the slice of interest in the target direction—a virtual fluoroscope.

Thus, in some embodiments, the techniques include determining, based on the first set of measurements, a different second background image for radiation transmitted through the body in a different second direction without the effects of the voxels in the slice of interest. Then a subsequent image is determined based on a subsequent measurement of radiation transmitted through the body in the second direction at a later time. A second difference is determined between the subsequent image and the second background image. A transformation is determined in a target direction of at least one of the first difference and the second difference to show a time rate of change in the slice of interest in the target direction.

In various embodiments, the target direction is the same as either the first direction or the second direction. In some embodiments, the target direction is different from both the first direction and the second direction.

Figure 10:
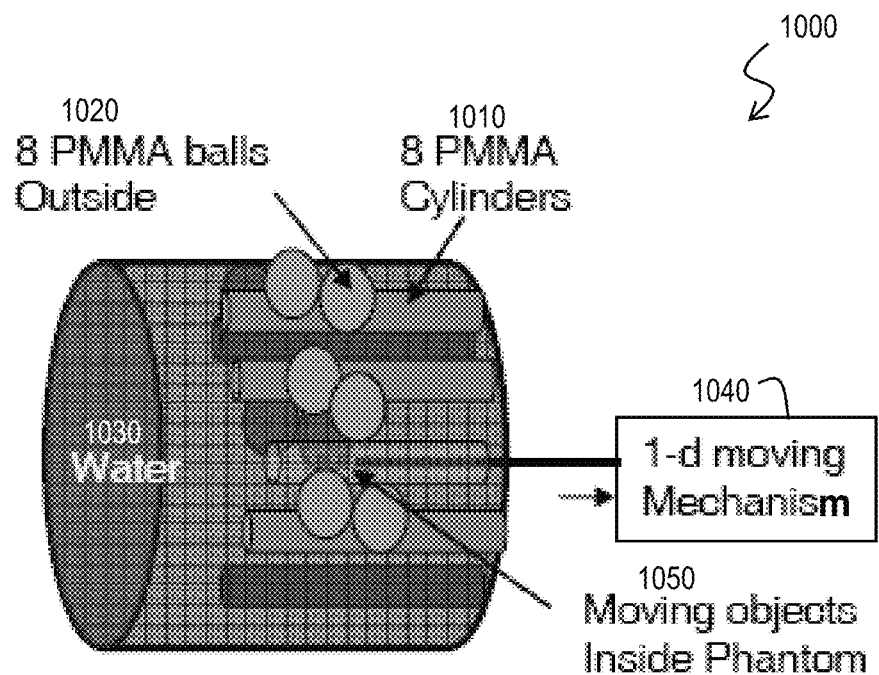
FIG. 10 is a block diagram that illustrates an example physical arrangement to generate an image phantom for demonstrating one or more steps of the method of FIG. 5 to determine motion in the SOI, according to an embodiment.

In an experimental embodiment, a subject included a phantom comprising a 14 centimeter (cm, 1 cm=$10^{-2}$ meters) diameter cylindrical water vessel containing objects subject to one-dimensional cyclic motion. FIG. 10 is a block diagram that illustrates an example physical arrangement to generate an image phantom 1000 for demonstrating one or more steps of the method of FIG. 5 to determine motion in the SOI, according to an embodiment. The phantom 1000 includes eight PMMA balls 1020 outside 8 PMMA cylinders 1010 in water 1030. The image phantom 1000 also includes objects 1050 inside the phantom that are moved by a one dimensional (1-d) moving mechanism 1040 that causes the object 1050 to move inside the image phantom 1000.

Figure 11:
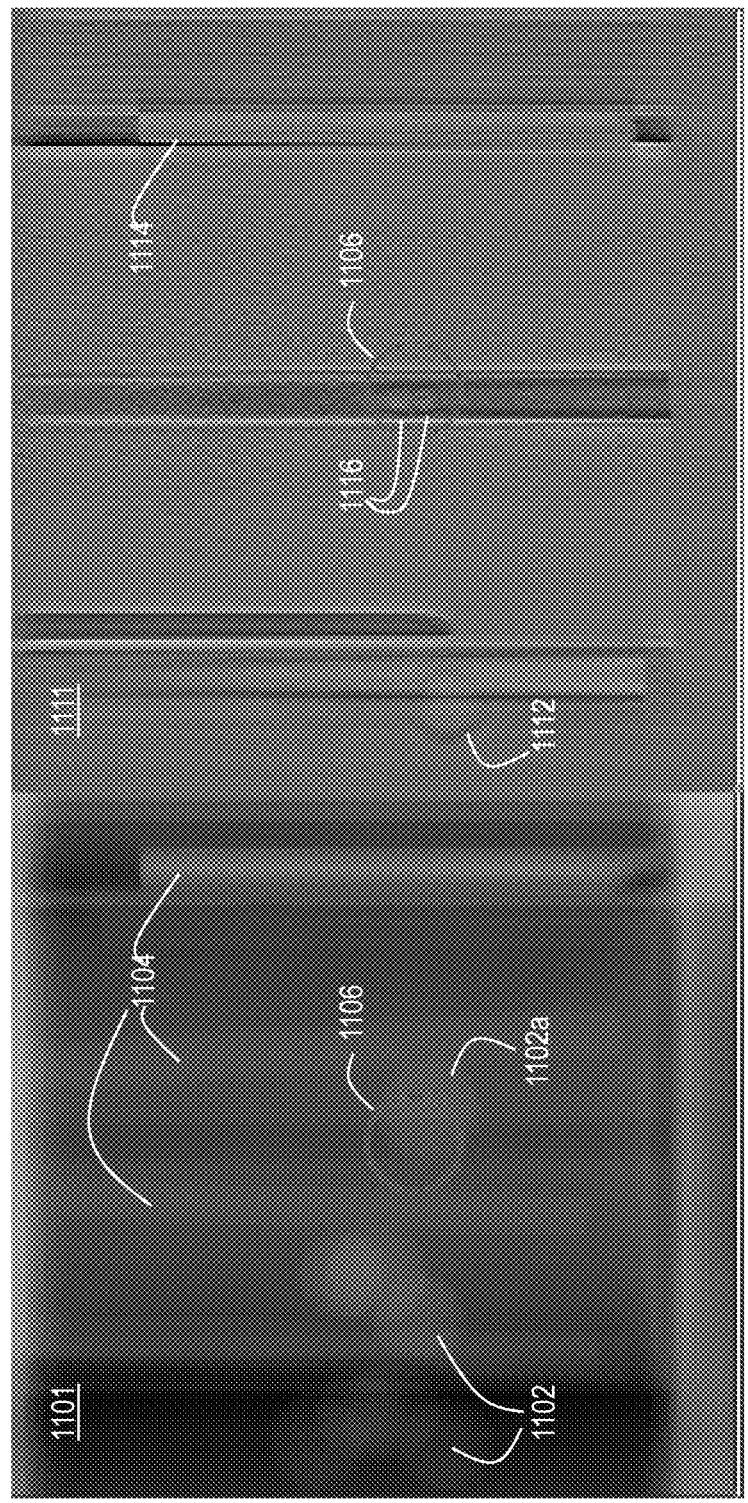
FIG. 11 is a pair of images that illustrate example improvement provided by tomographic image via background subtraction (TIBS), according to an embodiment.

This phantom is used to test the feasibility of the fluoroscopy imaging of a planar slice of interest (SOI). Outside the phantom, seven cylinders, each with a diameter of 1 cm, and eight balls, each of 2.5 cm diameter, were attached to decrease subject contrast. All of the balls and cylinders are made of the transparent thermoplastic Poly(methyl methacrylate) (PMMA). Two balls, each of one half centimeter diameter, were used as moving objects. One of the balls is made of high density polyethylene and the other is Polyoxymethylen, Formaldehyde Homopolymer (POM) Acetal Homopolymer plus polytetrafluoroethylen (PTFE) which goes by the tradename DERLIN. A short scan CBCT image is acquired and the projection images of the CBCT were used for this experiment. The slice of interest includes the half cm diameter balls. Thus, in this embodiment, the first set of measurements and the current measurement and the subsequent measurement are all acquired from a kilovoltage X-ray cone beam source mounted on a gantry for radiation at a plurality of directions FIG. 11 is a pair of images that illustrate example improvement provided by tomographic image via background subtraction (TIBS), according to an embodiment. This embodiment is the experimental embodiment described above. The first image 1101 shows a 2D projection image before background subtraction. The 1 cm diameter cylinders 1101 and 2.5 cm diameter balls 1102 are evident. The two half cm diameter balls are in region 1106, but are not readily visible, obscured by an intervening 2.5 cm diameter ball 1102a. The second image 1111 shows a 2D projection image after background subtraction. The 1 cm diameter cylinders 1111 and 2.5 cm diameter balls 1112 in the slice of interest are evident. The two half cm diameter balls in region 1116 are also evident with higher contrast than in image 1101. The effect of ball 1102a has been removed.

Image 1101 is a cross sectional image of viewing angle at 270 degrees acquired from a projection image of the same beam angle. Image 1111 is the X-ray projection image of the viewing angle with background subtracted taken at a different beam angle. Contrast of all objects is improved in the SOI because background objects such as balls and cylinders in other portions of the subject are removed. The thickness of the SOI was chosen to be 1 cm to generate the tomographic quality, high contrast image 1111. This embodiment shows that the cross sectional images for any desired viewing angle can be obtained while the X-ray source is pointed in a different direction. Thus many gantry angles around the desired viewing angle can be chosen to acquire the SOI image.

Figure 12:
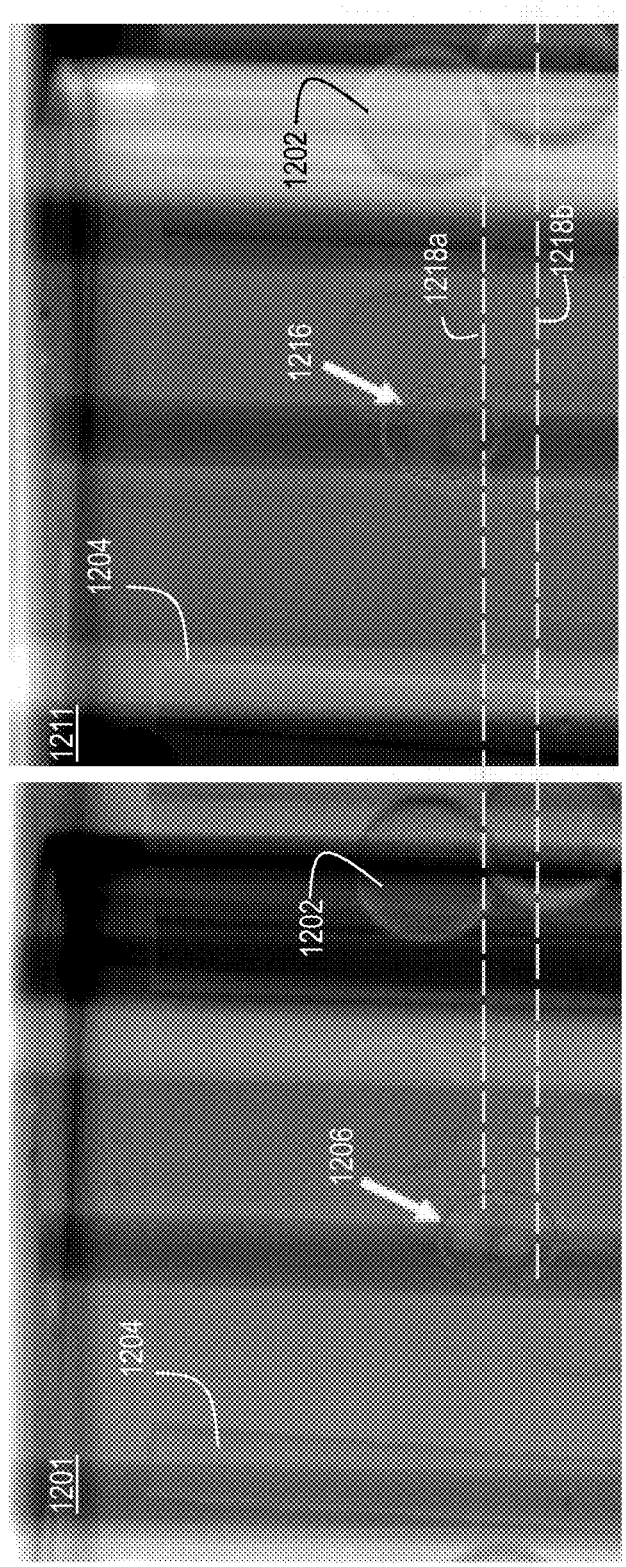
FIG. 12 is a pair of images that illustrate example motion detection using TIBS, according to an embodiment.

FIG. 12 is a pair of images that illustrate example motion detection using TIBS, according to an embodiment. This embodiment is the experimental embodiment described above. The first image 1201 shows a 2D projection image after background subtraction at a first time. The 1 cm diameter cylinders 1204 and 2.5 cm diameter balls 1202 in the slice of interest are evident. The two half cm diameter balls in region 1206 are also evident. The second image 1211 shows a 2D projection image in the same viewing direction after background subtraction at a subsequent time (and different beam direction). The 1 cm diameter cylinders 1204 and 2.5 cm diameter balls 1202 in the slice of interest are evident. The two half cm diameter balls in region 1216 are also evident. The positions of the two half cm diameter balls have changed; and, thus, region 1216 is displaced upward in FIG. 12 from the location of region 1206. The positions of the two balls in image 1201 are extended to image 1211 by dashed lines 1218a and 1218b, respectively, to make the detected motion more apparent.

FIG. 12 shows the different position of the objects of the same viewing angle taken at different times from different beam angles. While the actual background signal is not completely removed (e.g., traces of balls and cylinders due to different gantry angles are still evident to some degree), the effects of objects outside the SOI are significantly reduced.

The fluoroscope-like images of the moving objects was acquired by combining the SOI images from different gantry angles at different time. Breathing surrogates or sorting processes are not needed in order to generate tomographic quality images of moving objects, because those images are acquired directly from the projection images. Projection images are acquired while the body is on the table. Fluoroscopic image of SOI can be obtained in real time using the new method presented in this embodiment.

Using such techniques, moving objects in complex structures are observed while the background objects are removed or significantly reduced. To setup the body accurately and to evaluate the tumor motion are very important tasks in radiation treatment. The experimental embodiment suggests that the technique can be applied to determine the tumor position and motion in real time for the cases in which a tumor is moving during treatment, such as with tumors in the lung.

7. Hardware Overview

Figure 13:
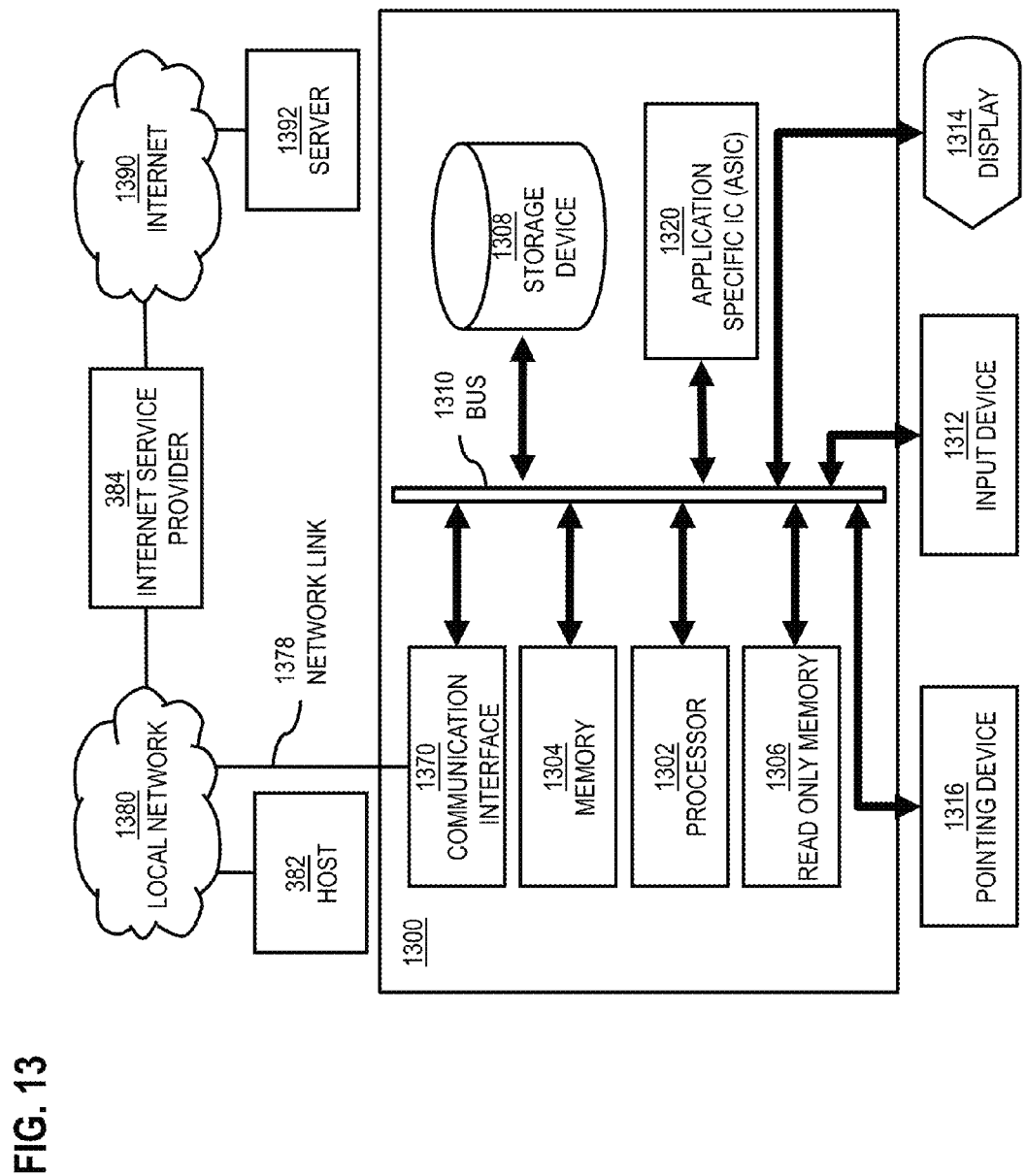
FIG. 13 is a block diagram that illustrates an example computer system upon which an embodiment of the invention may be implemented.

FIG. 13 is a block diagram that illustrates a computer system 1300 upon which an embodiment of the invention may be implemented. Computer system 1300 includes a communication mechanism such as a bus 1310 for passing information between other internal and external components of the computer system 1300. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1300, or a portion thereof, constitutes a means for performing one or more steps of one or more methods described herein.

A sequence of binary digits constitutes digital data that is used to represent a number or code for a character. A bus 1310 includes many parallel conductors of information so that information is transferred quickly among devices coupled to the bus 1310. One or more processors 1302 for processing information are coupled with the bus 1310. A processor 1302 performs a set of operations on information. The set of operations include bringing information in from the bus 1310 and placing information on the bus 1310. The set of operations also typically include comparing two or more units of information, shifting positions of units of information, and combining two or more units of information, such as by addition or multiplication. A sequence of operations to be executed by the processor 1302 constitute computer instructions.

Computer system 1300 also includes a memory 1304 coupled to bus 1310. The memory 1304, such as a random access memory (RAM) or other dynamic storage device, stores information including computer instructions. Dynamic memory allows information stored therein to be changed by the computer system 1300. RAM allows a unit of information stored at a location called a memory address to be stored and retrieved independently of information at neighboring addresses. The memory 1304 is also used by the processor 1302 to store temporary values during execution of computer instructions. The computer system 1300 also includes a read only memory (ROM) 1306 or other static storage device coupled to the bus 1310 for storing static information, including instructions, that is not changed by the computer system 1300. Also coupled to bus 1310 is a non-volatile (persistent) storage device 1308, such as a magnetic disk or optical disk, for storing information, including instructions, that persists even when the computer system 1300 is turned off or otherwise loses power.

Information, including instructions, is provided to the bus 1310 for use by the processor from an external input device 1312, such as a keyboard containing alphanumeric keys operated by a human user, or a sensor. A sensor detects conditions in its vicinity and transforms those detections into signals compatible with the signals used to represent information in computer system 1300. Other external devices coupled to bus 1310, used primarily for interacting with humans, include a display device 1314, such as a cathode ray tube (CRT) or a liquid crystal display (LCD), for presenting images, and a pointing device 1316, such as a mouse or a trackball or cursor direction keys, for controlling a position of a small cursor image presented on the display 1314 and issuing commands associated with graphical elements presented on the display 1314.

In the illustrated embodiment, special purpose hardware, such as an application specific integrated circuit (IC) 1320, is coupled to bus 1310. The special purpose hardware is configured to perform operations not performed by processor 1302 quickly enough for special purposes. Examples of application specific ICs include graphics accelerator cards for generating images for display 1314, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1300 also includes one or more instances of a communications interface 1370 coupled to bus 1310. Communication interface 1370 provides a two-way communication coupling to a variety of external devices that operate with their own processors, such as printers, scanners and external disks. In general the coupling is with a network link 1378 that is connected to a local network 1380 to which a variety of external devices with their own processors are connected. For example, communication interface 1370 may be a parallel port or a serial port or a universal serial bus (USB) port on a personal computer. In some embodiments, communications interface 1370 is an integrated services digital network (ISDN) card or a digital subscriber line (DSL) card or a telephone modem that provides an information communication connection to a corresponding type of telephone line. In some embodiments, a communication interface 1370 is a cable modem that converts signals on bus 1310 into signals for a communication connection over a coaxial cable or into optical signals for a communication connection over a fiber optic cable. As another example, communications interface 1370 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1370 sends and receives electrical, acoustic or electromagnetic signals, including infrared and optical signals, which carry information streams, such as digital data.

The term computer-readable medium is used herein to refer to any medium that participates in providing information to processor 1302, including instructions for execution. Such a medium may take many forms, including, but not limited to, non-volatile media, volatile media and transmission media. Non-volatile media include, for example, optical or magnetic disks, such as storage device 1308. Volatile media include, for example, dynamic memory 1304. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1302, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Logic encoded in one or more tangible media includes one or both of processor instructions on a computer-readable storage media and special purpose hardware, such as ASIC *320.

Network link 1378 typically provides information communication through one or more networks to other devices that use or process the information. For example, network link 1378 may provide a connection through local network 1380 to a host computer 1382 or to equipment 1384 operated by an Internet Service Provider (ISP). ISP equipment 1384 in turn provides data communication services through the public, world-wide packet-switching communication network of networks now commonly referred to as the Internet 1390. A computer called a server 1392 connected to the Internet provides a service in response to information received over the Internet. For example, server 1392 provides information representing video data for presentation at display 1314.

The invention is related to the use of computer system 1300 for implementing the techniques described herein. According to one embodiment of the invention, those techniques are performed by computer system 1300 in response to processor 1302 executing one or more sequences of one or more instructions contained in memory 1304. Such instructions, also called software and program code, may be read into memory 1304 from another computer-readable medium such as storage device 1308. Execution of the sequences of instructions contained in memory 1304 causes processor 1302 to perform the method steps described herein. In alternative embodiments, hardware, such as application specific integrated circuit 1320, may be used in place of or in combination with software to implement the invention. Thus, embodiments of the invention are not limited to any specific combination of hardware and software.

The signals transmitted over network link 1378 and other networks through communications interface 1370, carry information to and from computer system 1300. Computer system 1300 can send and receive information, including program code, through the networks 1380, 1390 among others, through network link 1378 and communications interface 1370. In an example using the Internet 1390, a server 1392 transmits program code for a particular application, requested by a message sent from computer 1300, through Internet 1390, ISP equipment 1384, local network 1380 and communications interface 1370. The received code may be executed by processor 1302 as it is received, or may be stored in storage device 1308 or other non-volatile storage for later execution, or both. In this manner, computer system 1300 may obtain application program code in the form of a signal on a carrier wave.

Various forms of computer readable media may be involved in carrying one or more sequence of instructions or data or both to processor 1302 for execution. For example, instructions and data may initially be carried on a magnetic disk of a remote computer such as host 1382. The remote computer loads the instructions and data into its dynamic memory and sends the instructions and data over a telephone line using a modem. A modem local to the computer system 1300 receives the instructions and data on a telephone line and uses an infra-red transmitter to convert the instructions and data to a signal on an infra-red a carrier wave serving as the network link 1378. An infrared detector serving as communications interface 1370 receives the instructions and data carried in the infrared signal and places information representing the instructions and data onto bus 1310. Bus 1310 carries the information to memory 1304 from which processor 1302 retrieves and executes the instructions using some of the data sent with the instructions. The instructions and data received in memory 1304 may optionally be stored on storage device 1308, either before or after execution by the processor 1302.

Figure 14:
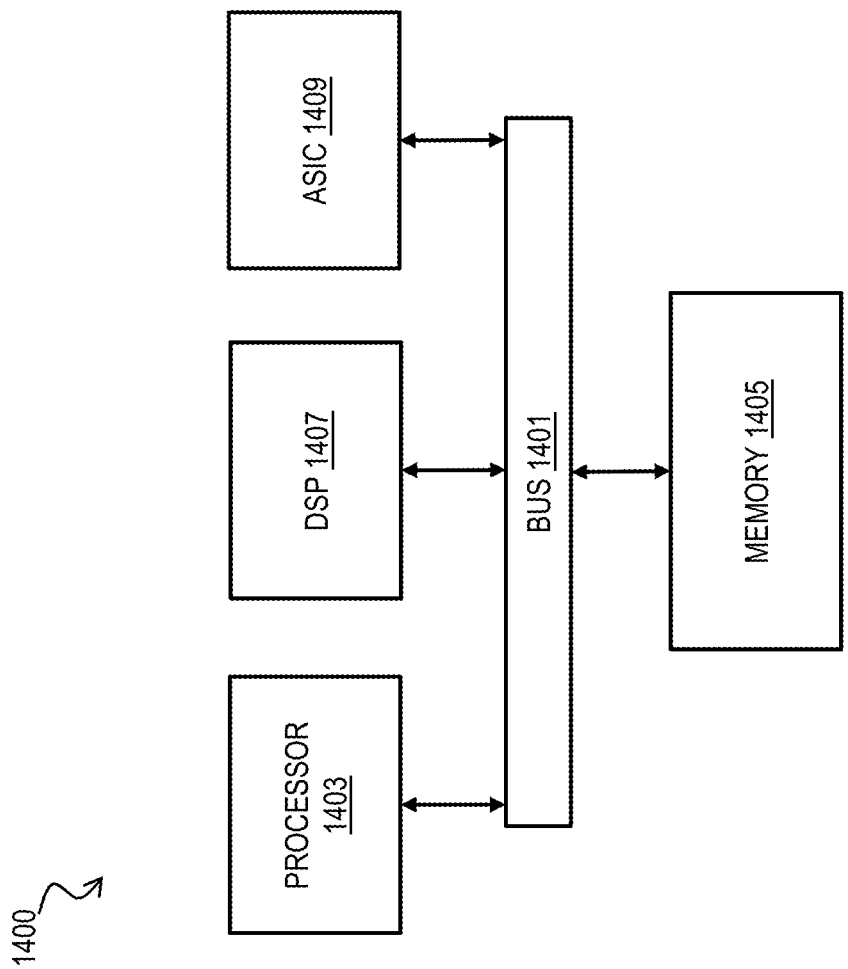
FIG. 14 illustrates a chip set upon which an embodiment of the invention may be implemented.

FIG. 14 illustrates a chip set 1400 upon which an embodiment of the invention may be implemented. Chip set 1400 is programmed to perform one or more steps of a method described herein and includes, for instance, the processor and memory components described with respect to FIG. 13 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1400, or a portion thereof, constitutes a means for performing one or more steps of a method described herein.

In one embodiment, the chip set 1400 includes a communication mechanism such as a bus 1401 for passing information among the components of the chip set 1400. A processor 1403 has connectivity to the bus 1401 to execute instructions and process information stored in, for example, a memory 1405. The processor 1403 may include one or more processing cores with each core configured to perform independently. A multi-core processor enables multiprocessing within a single physical package. Examples of a multi-core processor include two, four, eight, or greater numbers of processing cores. Alternatively or in addition, the processor 1403 may include one or more microprocessors configured in tandem via the bus 1401 to enable independent execution of instructions, pipelining, and multithreading. The processor 1403 may also be accompanied with one or more specialized components to perform certain processing functions and tasks such as one or more digital signal processors (DSP) 1407, or one or more application-specific integrated circuits (ASIC) 1409. A DSP 1407 typically is configured to process real-world signals (e.g., sound) in real time independently of the processor 1403. Similarly, an ASIC 1409 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1403 and accompanying components have connectivity to the memory 1405 via the bus 1401. The memory 1405 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1405 also stores the data associated with or generated by the execution of one or more steps of the methods described herein.

8. Extensions and Alternatives

Results with phantoms and a clinical case show that the TIBS technique effectively reduces ambiguities and enhances contrast over conventional kV imaging. The TIBS technique can provide excellent contrast for a section of an object with snapshot x-ray projections, therefore reducing the need for frequent uses of CT scans that requires excessive imaging time and dose for image guided radiation treatments In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method comprising:
   determining voxels in a slice of interest in a three dimensional computed tomography scan of the interior of a body based on a first set of measurements of radiation transmitted through the body;
   determining, based on the first set of measurements, a first background image for radiation transmitted through the body in a first direction without the effects of the voxels in the slice of interest;
   determining a current image based on a different current measurement of radiation transmitted through the body in the first direction; and
   determining a first difference between the current image and the first background image to show contrast in the slice of interest.

2. A method as recited in claim 1, further comprising transforming the first difference to a transformed difference in a different direction from the first direction.

3. A method as recited in claim 1, further comprising registering the current image to the first background image before determining the first difference between the current image and the first background image.

4. A method as recited in claim 1, further comprising:
   determining, based on the first set of measurements, a different second background image for radiation transmitted through the body in a different second direction without the effects of the voxels in the slice of interest;
   determining a subsequent image based on a subsequent measurement of radiation transmitted through the body in the second direction at a later time;
   determining a second difference between the subsequent image and the second background image; and
   transforming, to a target direction, at least one of the first difference and the second difference to show a time rate of change in the slice of interest in the target direction.

5. A method as recited in claim 4, wherein the target direction is the same as the first direction.

6. A method as recited in claim 4, wherein the target direction is the same as the second direction.

7. A method as recited in claim 4, wherein the target direction is different from both the first direction and the second direction.

8. A method as recited in claim 4, wherein the first set of measurements and the current measurement and the subsequent measurement are acquired from a kilovoltage X-ray cone beam source mounted on a gantry for radiation at a plurality of directions.

9. A non-transitory computer-readable medium carrying one or more sequences of instructions, wherein execution of the one or more sequences of instructions by one or more processors causes an apparatus to:
   determine voxels in a slice of interest in a three dimensional computed tomography scan of the interior of a body based on a first set of measurements of radiation transmitted through the body;
   determine, based on the first set of measurements, a first background image for radiation transmitted through the body in a first direction without the effects of the voxels in the slice of interest;
   determine a current image based on a different current measurement of radiation transmitted through the body in the first direction; and
   determine a first difference between the current image and the first background image.

10. A non-transitory computer-readable medium as recited in claim 9, wherein the apparatus is further caused to transform the first difference to a transformed difference in a different direction from the first direction.

11. A non-transitory computer-readable medium as recited in claim 9, wherein the apparatus is further caused to register the current image to the first background image before determining the first difference between the current image and the first background image.

12. A non-transitory computer-readable medium as recited in claim 9, wherein the apparatus is further caused to:
   determine, based on the first set of measurements, a different second background image for radiation transmitted through the body in a different second direction without the effects of the voxels in the slice of interest;
   determine a subsequent image based on a subsequent measurement of radiation transmitted through the body in the second direction at a later time;

determine a second difference between the subsequent image and the second background image; and transform, to a target direction, at least one of the first difference and the second difference to show a time rate of change in the slice of interest in the target direction.

13. A non-transitory computer-readable medium as recited in claim 12, wherein the target direction is the same as the first direction.

14. A non-transitory computer-readable medium as recited in claim 12, wherein the target direction is the same as the second direction.

15. A non-transitory computer-readable medium as recited in claim 12, wherein the target direction is different from both the first direction and the second direction.

16. A non-transitory computer-readable medium as recited in claim 12, wherein the first set of measurements and the current measurement and the subsequent measurement are acquired from a kilovoltage X-ray cone beam source mounted on a gantry for radiation at a plurality of directions.

17. An apparatus comprising:
    means for determining voxels in a slice of interest in a three dimensional computed tomography scan of the interior of a body based on a first set of measurements of radiation transmitted through the body;
    means for determining, based on the first set of measurements, a first background image for radiation transmitted through the body in a first direction without the effects of the voxels in the slice of interest;
    means for determining a current image based on a different current measurement of radiation transmitted through the body in the first direction; and
    means for determining a first difference between the current image and the first background image.

18. An apparatus as recited in claim 17, further comprising means for transforming the first difference to a transformed difference in a different direction from the first direction.

19. An apparatus as recited in claim 17, further comprising means for registering the current image to the first background image before determining the first difference between the current image and the first background image.

20. An apparatus as recited in claim 17, further comprising:
    means for determining, based on the first set of measurements, a different second background image for radiation transmitted through the body in a different second direction without the effects of the voxels in the slice of interest;
    means for determining a subsequent image based on a subsequent measurement of radiation transmitted through the body in the second direction at a later time;
    means for determining a second difference between the subsequent image and the second background image; and
    means for transforming, to a target direction, at least one of the first difference and the second difference to show a time rate of change in the slice of interest in the target direction.

* * * * *